(12) United States Patent
Maurette

(10) Patent No.: US 9,545,358 B2
(45) Date of Patent: Jan. 17, 2017

(54) CERVICAL SHIELD SEXUAL AID DEVICE AND METHOD FOR USE DURING INTERCOURSE

(71) Applicant: Neil L. Maurette, Calgary (CA)

(72) Inventor: Neil L. Maurette, Calgary (CA)

( * ) Notice: Subject to any disclaimer, the term of this patent is extended or adjusted under 35 U.S.C. 154(b) by 126 days.

(21) Appl. No.: 14/411,914

(22) PCT Filed: Apr. 9, 2013

(86) PCT No.: PCT/CA2013/050280
§ 371 (c)(1),
(2) Date: Dec. 30, 2014

(87) PCT Pub. No.: WO2013/152442
PCT Pub. Date: Oct. 17, 2013

(65) Prior Publication Data
US 2015/0190305 A1    Jul. 9, 2015

(30) Foreign Application Priority Data
Apr. 11, 2012   (CA) ..................................... 2774254

(51) Int. Cl.
*A61F 6/06*      (2006.01)
*A61H 19/00*    (2006.01)
*A61F 6/08*      (2006.01)

(52) U.S. Cl.
CPC .................. *A61H 19/50* (2013.01); *A61F 6/08* (2013.01); *A61H 2201/01* (2013.01)

(58) Field of Classification Search
CPC .................................. A61H 19/50; A61F 6/08
USPC .................................................. 128/830, 841
See application file for complete search history.

(56) References Cited

U.S. PATENT DOCUMENTS

| | | | | |
|---|---|---|---|---|
| 2,310,564 A | * | 2/1943 | Younkins | A61F 6/08 128/837 |
| 3,371,664 A | * | 3/1968 | Pleshette | A61F 6/08 128/837 |
| 4,381,771 A | | 5/1983 | Gabbay | |
| 4,703,752 A | * | 11/1987 | Gabbay | A61F 6/08 128/841 |
| 5,771,900 A | * | 6/1998 | Austin | A61F 6/08 128/830 |
| 2009/0281373 A1 | * | 11/2009 | Mark | A61H 19/34 600/38 |

* cited by examiner

*Primary Examiner* — Kristen Matter

(57) ABSTRACT

A sexual aid device comprising a main body (100) and a cervical void (110), sized and shaped to shield a cervix (350) during intercourse. This self-retaining device comprises a means to prevent a penis from colliding with the cervix (350), a means to shield the anterior vagina wall from frictional contact during sexual intercourse and at least one means to retain the sexual aid device within the vagina. This device provides a non-surgical, cost-effective solution to allow for more comfortable deeper penetration by guiding the penis away from the cervix.

18 Claims, 8 Drawing Sheets

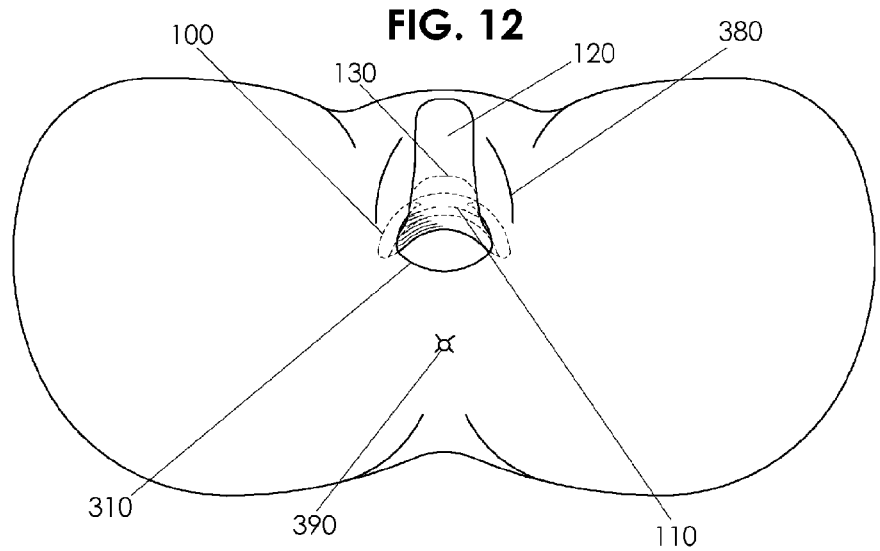
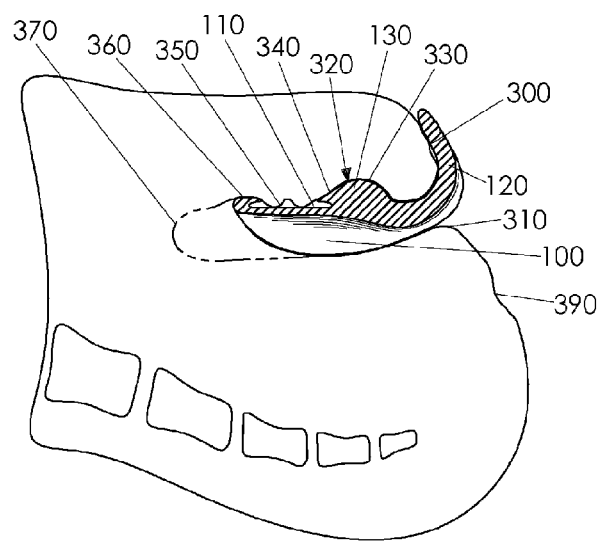
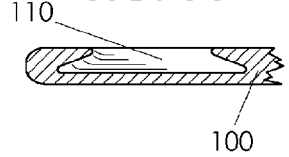
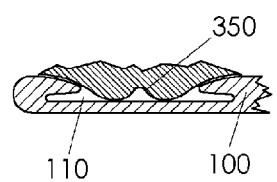

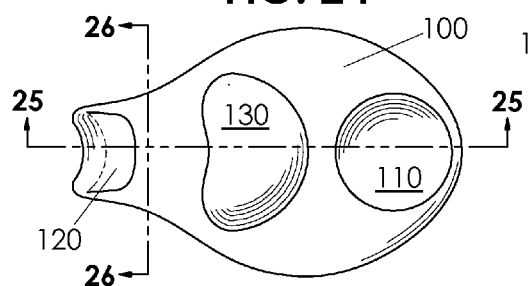
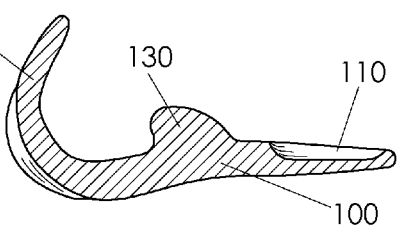
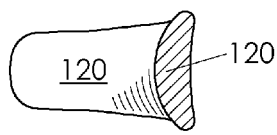
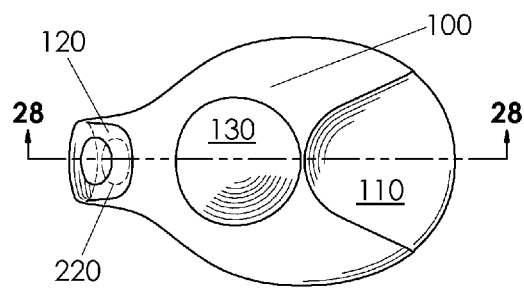
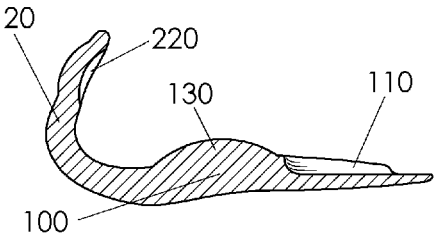
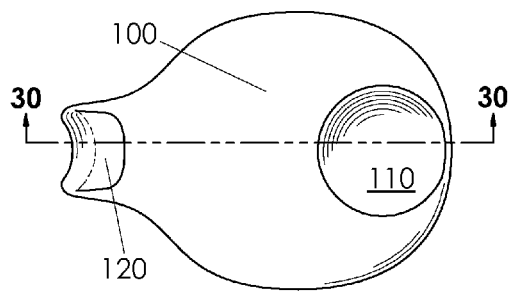
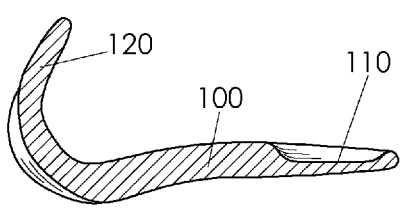

CERVICAL SHIELD SEXUAL AID DEVICE AND METHOD FOR USE DURING INTERCOURSE

BACKGROUND

Field

This application relates to sexual aids. In particular, a cervical shield device to be worn during intercourse to prevent an artificial or real human penis from colliding with a human cervix and to provide a guide to channel the penis away from the cervix to allow for more comfortable deeper penetration.

All instances of penis below refer to an artificial or real human penis.

Prior Art

There is little prior art pertaining to sexual aid devices used by individuals or couples to prevent collision dyspareunia (pain in the pelvic area from the penis colliding with the cervix during intercourse). The following prior art demonstrates the state of the art closest to the cervical shield sexual aid device and method.

U.S. Pat. No. 4,920,986, issued May 1, 1990 to Biswas, URINARY INCONTINENCE DEVICE, illustrates an intravaginal device to aid in controlling urinary incontinence. This device lines the vagina with a spongy material, thereby effectively shortening the depth of the vagina, preventing or restricting deeper penetration. The Biswas device distributes the impact from the penis over the cervix and the vaginal walls, exacerbating pain in the pelvic area instead of guiding the penis in a channel away from the cervix.

U.S. Pat. No. 6,503,190 B1, issued Jan. 7, 2003 and U.S. Pat. No. 6,645,137 B2, issued Nov. 11, 2003 to Ulmsten et al., VAGINAL PESSARY, describe a flexible body in the form of a belt or a split cylinder that may be coiled to be inserted into a vagina and as the flexible body expands, the body presses against the vaginal wall. While this pessary takes advantage of the resiliency of the material to self-retain, it does not cradle the cervix and does not create a channel to guide the penis away from the cervix for more comfortable deeper penetration. Furthermore, this pessary is not designed for intercourse; it creates unnatural sensations for the male and limits the wearer's sexual experience from a lack of sensations on the vaginal walls.

U.S. Pat. No. 7,931,605, issued Apr. 26, 2011, ELECTRO-MECHANICAL SEXUAL STIMULATION DEVICE, USD605779 issued Dec. 8, 2009 and USD652942 issued Jan. 24, 2012, to Murison, describe a stimulation device that has an inner arm dimensioned for insertion into the vagina, and an outer arm for contact with the clitoris. Murison's device does not extend past the anterior fornix and does not cradle the cervix in a void of material nor does the device channel the penis away from colliding with the cervix to allow for more comfortable deeper penetration. Murison's device does not unfurl within the vagina and nor does it allow the device to be self-retained exclusively by the vagina. Murison's device lacks shape geometry to utilize the cervix to locate and position the device and furthermore lacks shape geometry to prevent movement of the device during intercourse. Murison's device does not initiate a natural tendency to refurl when an external force is applied to the device allowing for ease of removal.

Pub. No. US 2009/0281373 A1, filed Dec. 20, 2007, to Mark, SEXUAL AID DEVICE AND METHOD, discloses a device to occupy space within a vagina. Mark's device does not comfortably locate and position itself on the cervix. Marks's device does not cradle the cervix in a void of material, minimizing pressure on the cervix, allowing the penis to go past the cervix for more comfortable deeper penetration. Additionally, Mark's device lacks shape geometry to utilize the cervix to locate and position the device and furthermore lacks shape geometry to prevent movement of the device during intercourse. Mark's device does not furl for ease of insertion into the vagina nor does Mark's device initiate a natural tendency to refurl when an external force is applied for ease of removal.

Pat. No. CA 2691663, issued Nov. 15, 2011, to Maurette, FEMALE POSTERIOR WALL PROSTHESIS, discloses a prosthesis that shields the posterior vaginal wall. This prosthesis is not designed to fit on the anterior vaginal wall and to locate and position itself on the cervix. Wearing this prosthesis on the anterior vaginal wall causes shifting of the prosthesis about the cervix, irritating the cervix. The prosthesis applies additional pressure to the cervix as there is no material void to cradle the cervix and support the device from movement during intercourse. Furthermore, the prosthesis lacks shape geometry to utilize the cervix for locating, positioning and retaining the prosthesis within the vagina, eliminating the need for a specialized flared flattened handle, which would simplify and improve the prosthesis.

U.S. Pat. No. 3,996,930, issued Dec. 14, 1976, to Sekulich, SELF-CONTAINED GYNECOLOGIC STIMULATOR, describes a resilient V-shaped stimulator with a posterior leg with an elongated trough for receipt of the clitoris. Sekulich's stimulator does not shield the cervix or comfortably guide the penis past the cervix with the least amount of pressure applied to the cervix to allow for more comfortable deeper penetration intercourse. Sekulich's stimulator lacks shape geometry to prevent it from sliding from side to side over the cervix within the vagina, irritating the cervix. Sekulich's device does not cradle the cervix or create a channel to guide the penis away from the cervix allowing for more comfortable deeper penetration. Sekulich's device does not furl for ease of insertion into the vagina nor does Sekulich's device initiate a natural tendency to refurl when an external force is applied to the device allowing for ease of removal.

Pat. No. GB 2413768B, issued Jun. 12, 2006, to Foks and Dawe, SEX AID TO PREVENT FULL PENETRATION DURING SEXUAL INTERCOURSE, describes a sex aid worn outside the body on the male, limiting the depth of penetration during intercourse. It serves as a spacer between the penis base and a vaginal entrance. This sex aid does not cradle the cervix or create a channel to guide the penis away from the cervix allowing for more comfortable deeper penetration.

There is a need for a shielding device that can be worn on the anterior vaginal wall during coitus to shield against collision contact between the penis and the cervix and to provide a guide to channel the penis away from the cervix to allow for more comfortable deeper penetration.

OBJECTS AND ADVANTAGES

Accordingly, several objects and advantages of the cervical shield sexual aid device and method are to provide a:

(a) shield that has a positioning means to locate the shield on a cervix;

(b) shield that guides a penis away from a cervix to prevent painful intercourse, allowing for more comfortable deeper penetration;

(c) channel for guiding a penis away from a cervix;

(d) shield that has design features to ensure that the shield remains in place on the anterior vagina wall;

(e) shield that naturally unfurls after insertion into the vagina providing the necessary tension in its unfurling state to self-retain and remain in place;

(f) shield for an anterior vaginal wall to protect a sensitive area against frictional contact;

(g) shield for a penis to prevent painful collision with a cervix;

(h) shield to provide urinary incontinence relief during intercourse and that is comfortable for both partners, while maximizing sensations for both partners;

(i) shield to restore vaginal volume on the anterior vaginal wall while comfortably protecting a cervix from being struck by a penis;

(j) shield that rolls into a cylindrical tube-like shape that allows for ease of insertion into the vagina;

(k) shield that has a natural tendency to refurl when an external force is applied to the shield allowing for ease of removal from the vagina;

(l) shield made with a soft elastomeric material to comfortably surround a cervix and to mimic the tactile feel of the inside of the vagina;

(m) device which resists rotation after being positioned on a cervix.

Further objects and advantages will become apparent from a consideration of the ensuing descriptions and drawings.

SUMMARY

The cervical shield sexual aid device and method provide a means of shielding the cervix and guiding the penis to avoid collision with the cervix allowing for more comfortable deeper penetration during intercourse. A shield comprises at least one main body sized to cover the anterior vaginal wall and at least one cervical void to position and locate the device on the cervix. Additionally, the shield can have none, one, or a plurality of the following elements in various combinations and configurations comprising: arms, protrusions, grooves, recesses, stiffeners, clitoral exciters, textures and stimulation devices. The shield is designed to be curled by hand for ease of insertion into the vagina, to self-align onto the cervix and to self-retain as the device naturally unfurls. The cervical shield sexual aid device offers an inexpensive solution to addressing collision dyspareunia while enabling more comfortable deeper penetration.

DRAWINGS

Figures

FIG. 12 is an axial view showing the shield of FIG. 10 positioned in the vagina.

FIG. 13 is a sagittal view showing the shield of FIG. 10 positioned in the vagina with a phantom line showing an extended vaginal passage from deeper penetration.

FIG. 14 is a partial cross-section view of an alternative shield showing a noncollapsed cervical void.

FIG. 15 is the partial cross-section view of FIG. 14 showing a collapsed cervical void inducing a suction effect in position onto the cervix.

FIG. 24 is a top view of the shield of FIG. 2 with an alternative main body, an alternative cervical void and an alternative protrusion.

FIG. 25 is a cross-sectional view taken along line 25-25 of FIG. 24.

FIG. 26 is a cross-sectional view taken along line 26-26 of FIG. 24.

FIG. 27 is a top view of a variation of the shield of FIG. 2 with an alternative cervical void, an alternative arm, an alternative protrusion, and a clitoral exciter.

FIG. 28 is a cross-sectional view taken along line 28-28 of FIG. 27.

FIG. 29 is a top view of a variation of the shield of FIG. 2 with an alternative main body, an alternative cervical void and no protrusion.

FIG. 30 is a cross-sectional view taken along line 30-30 of FIG. 29.

Figure 1:
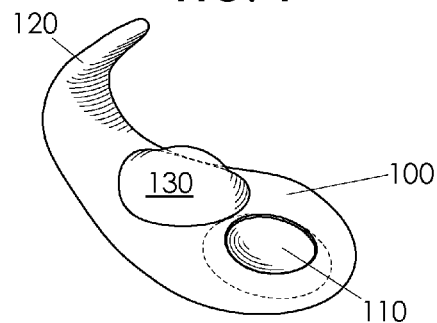
FIG. 1 is an isometric view of the shield.
Figure 2:
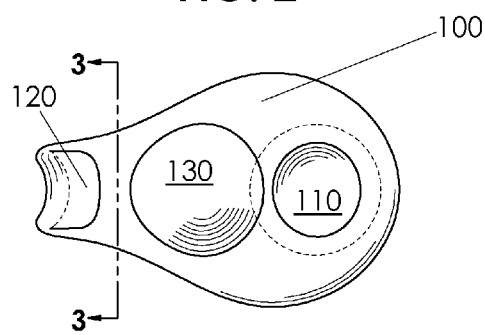
FIG. 2 is a top view of the shield of FIG. 1.
Figure 3:
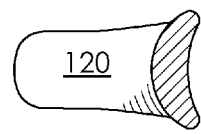
FIG. 3 is a cross-sectional view taken along line 3-3 of FIG. 2.
Figure 4:
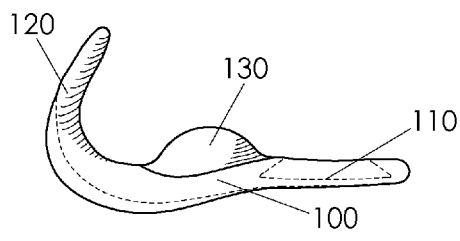
FIG. 4 is a side view of the shield of FIG. 2.
Figure 5:
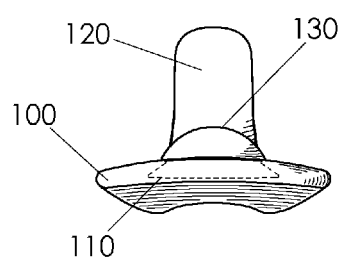
FIG. 5 is an end view of the shield of FIG. 4.
Figure 6:
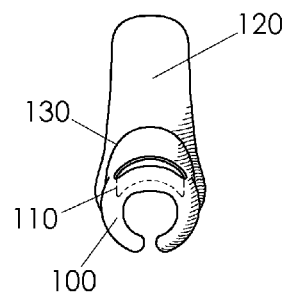
FIG. 6 is an end view of the shield of FIG. 4 in a furled state.
Figure 7:
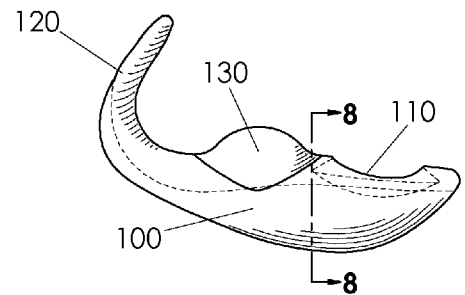
FIG. 7 is a side view of the shield of FIG. 6.
Figure 8:
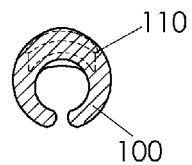
FIG. 8 is a cross-sectional view taken along line 8-8 of FIG. 7.
Figure 9:
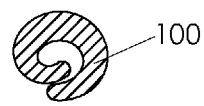
FIG. 9 is an alternative cross-sectional view showing a more tightly furled shield.

REFERENCE NUMERALS 100 main body
110 cervical void
120 arm
130 protrusion
140 groove
200 recess
210 stiffener
220 clitoral exciter
230 texture
300 clitoris
310 vaginal entrance
320 anterior vaginal wall
330 G-spot (Gräfenberg spot)
340 anterior fornix
350 cervix
360 posterior fornix
370 stretched vaginal wall
380 labia majora
390 anus
400 stimulation device A cervical shield sexual aid device comprises at least one main body 100 and at least one cervical void 110 and none, one or a plurality of additional elements. This shield, when inserted into a vagina protects the cervix 350 from collision with the penis and creates a channel for movement of the penis away from the cervix 350.

DETAILED DESCRIPTION

FIGS. 1-52

Figure 52:
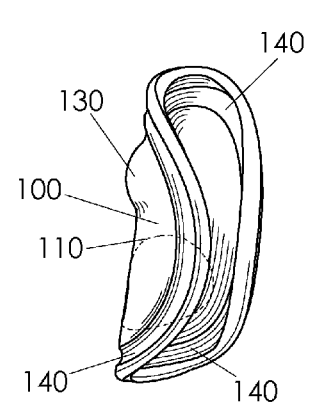
FIG. 52 is an isometric view of the shield of FIG. 50 in a coiled state.

The cervical shield sexual aid device generally resembles a flattened shape with a void as illustrated in FIGS. 1-52. The shield features variations of the following components comprising: a main body 100, a cervical void 110, and none, one or a plurality of arms 120, protrusions 130, grooves 140, recesses 200, stiffeners 210, clitoral exciters 220, textures 230 and stimulation devices 400.

Main Body 100—

Figure 10:
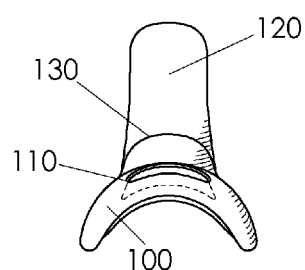
FIG. 10 is an end view of the shield of FIG. 4 representing the unfurled state within a vagina.
Figure 11:
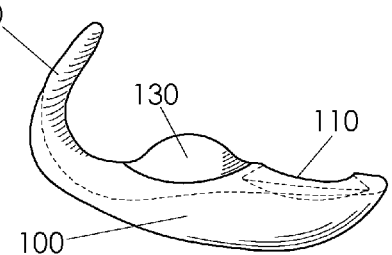
FIG. 11 is a side view of the shield of FIG. 10.

As illustrated in FIGS. 1-5 the shield has a main body 100. The main body 100 generally resembles an ellipse and is comprised of a resilient elastomeric material deformable by hand. The main body 100 is coiled for ease of insertion into the vagina. The end of the main body 100 which is inserted into the vagina first is generally curved for ease of insertion. The other end of the main body 100 is shaped to allow the device to naturally pull into the vagina once it passes the vaginal entrance 310 during unfurling and allowing for refurling when the main body 100 exits the vagina. The main body 100 furls away from the anterior vaginal wall 320. The main body 100 is resilient, unfurling within the vagina and applying pressure to the walls of the vagina, holding the shield in place and resisting displacement. Complete unfurling is not necessary. The main body 100, when in place within the vagina, create a crescent-shaped channel for intercourse, as in FIGS. 10, 12. When in position within the vagina, the main body 100: shields the cervix 350 from collision by the penis; provides a channel for guiding the penis away from the cervix 350 allowing for more comfortable deeper penetrating intercourse (as in FIG. 13); serves as a retention means to retain the shield within the vagina; shields against frictional contact on the anterior vaginal wall 320; guides the penis away from the anterior vaginal wall 320; resists bending; resists displacement; offers structure and a means of attachment for other additional elements of the shield; and applies pressure to the vaginal walls offering relief from urinary incontinence during intercourse.

Figure 36:
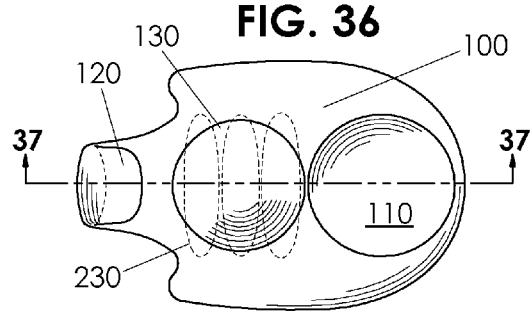
FIG. 36 is a top view of a variation of the shield of FIG. 2 with an alternative main body, an alternative cervical void, an alternative arm, an alternative protrusion and texture.
Figure 37:
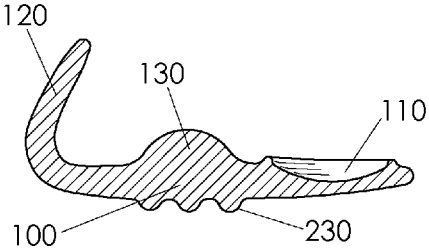
FIG. 37 is a cross-sectional view taken along line 37-37 of FIG. 36.

Alternatively, as illustrated in FIG. 36, the main body 100 can be spade-shaped to better retain the shield within the vagina. Due to the material properties, the spade points on the main body 100 flex and the main body 100 refurls when the shield is clasped and removed.

Figure 34:
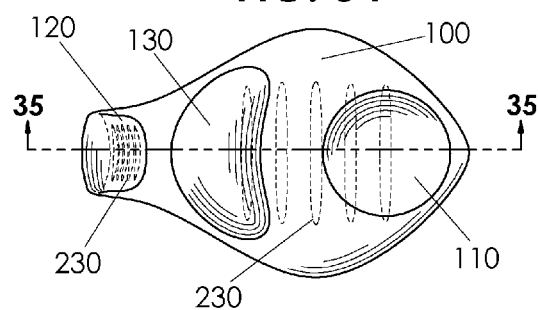
FIG. 34 is a top view of a variation of the shield of FIG. 2 with an alternative main body, an alternative cervical void, an alternative arm, an alternative protrusion and texture.
Figure 35:
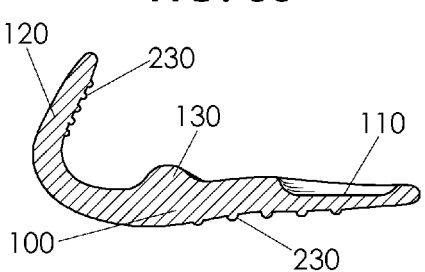
FIG. 35 is a cross-sectional view taken along line 35-35 of FIG. 34.
Figure 40:
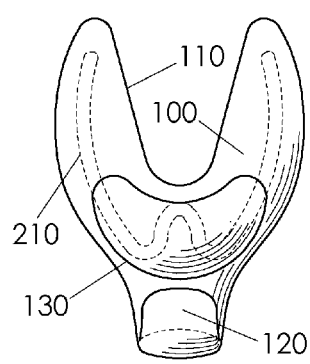
FIG. 40 is a top view of a variation of the shield of FIG. 2 with an alternative main body, an alternative cervical void, an alternative arm, an alternative protrusion, and a stiffener.

Variations of the main body 100 comprise: various sized main bodies; main bodies with various cross-sectional geometry; main bodies with edges of varying thicknesses; main bodies comprised of multiple pieces; main bodies with varying thicknesses; main bodies that are elliptical, diamond-shaped (e.g. FIG. 34), spade-shaped (e.g. FIG. 36), U-shaped (e.g. FIG. 40), generally round (e.g. FIG. 50), polygonal, hourglass-shaped, triangular, irregular-shaped and combinations thereof; main bodies comprising any shape that supports the functions to furl and unfurl, shield the cervix, and to apply pressure on the vaginal walls to resist displacement. The main body can have none, one or a plurality of arms, protrusions, grooves, recesses, stiffeners, textures, and stimulation devices. The shield has at least one main body.

Cervical Void 110—

As illustrated in FIGS. 1-52, the shield has a section of material removed from a portion of the main body 100: the cervical void 110. The cervical void 110 is dimensioned to shield, position and locate the device on the cervix 350 within the vagina. The cervical void 110 serves to shield the cervix 350 from painful collision by the penis. Due to the locating and positioning functions of the cervical void 110 there is no need for a flared enlarged arm on the outside of the vagina for retaining the shield.

Alternatively, as illustrated in FIGS. 1-30, 34-39, 41-44, 48-52, the cervical void 110 additionally serves to protect the cervix 350 from frictional contact by the penis.

Alternatively, the cervical void 110 can comprise a suction means. The size, shape and flexural characteristics of the cervical void 110 can allow for flexing of the cervical void 110 edges, inducing a vacuum effect onto the cervix 350 to further aid in holding the device in position on the wearer as in FIGS. 13, 15. In FIGS. 1-15 the cervical void 110 edge is shaped with an overhang to apply a suction effect. FIG. 14 shows the overhanging cervical void 110 edge in a relaxed/neutral state. When the penis moves over the main body 100 and subsequently passes the cervical void 110, the cervical void 110 ensures that the shield stays in place over the cervix 350.

Figure 31:
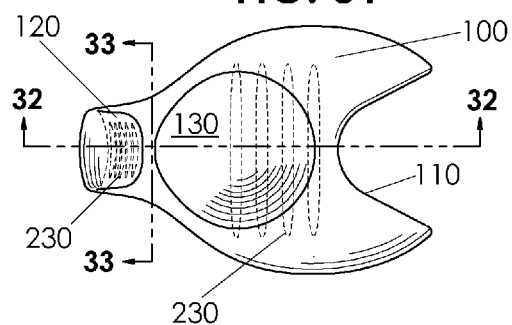
FIG. 31 is a top view of a variation of the shield of FIG. 2 with an alternative main body, an alternative cervical void, an alternative arm, an alternative protrusion and texture.
Figure 32:
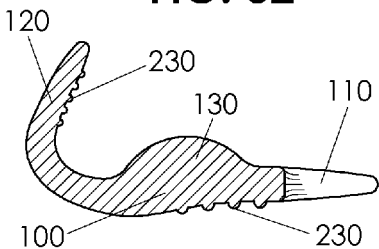
FIG. 32 is a cross-sectional view taken along line 32-32 of FIG. 31.
Figure 33:
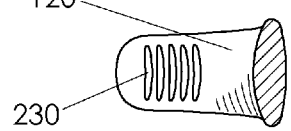
FIG. 33 is a cross-sectional view taken along line 33-33 of FIG. 31.

Variations of the cervical void 110 comprise: voids of various sizes; voids with various geometric concave shapes comprising: elliptical, polygonal, irregular, round and combinations thereof; voids with various sized overhanging edges (e.g. FIG. 14); voids of various depths; U-shaped voids (e.g. FIGS. 27, 31, 40); voids with various raised edge geometries (e.g. FIG. 37); voids lined with an alternate material; voids with none, one or a plurality of recesses, stiffeners, textures, and stimulation devices; voids that are angled from the main body (e.g. FIG. 48-49); voids comprising any shape that serves to surround the cervix for shielding, locating or positioning the device on the cervix. The shield has at least one cervical void.

Arm 120—

As illustrated in FIGS. 1-44, 48-49 the shield can have an extended elongated portion of material attached to the main body 100: the arm 120. The arm 120 connects to and extends from the main body 100 and curves towards the cervical void 110. When the shield is in place within the vagina, the arm 120 extends from the main body 100 and curves towards the mons pubis, and can reside close to the clitoris 300 as in FIGS. 12-13. The arm 120 is dimensioned to permit intercourse. The arm 120 cross-sectional perimeter does not increase in size from the main body 100 through to the tip of the arm 120. The arm 120 provides a means to grasp the shield for adjusting, positioning, and/or removing. The arm 120 can serve to translate the movement of the penis in the vagina to vibrational movement on the clitoris 300.

Variations of the arm 120 comprise: various sized arms; arms with various cross-sectional geometry: round, polygonal, crescent-shaped (e.g. FIGS. 3, 26), irregular, elliptical (e.g. FIG. 33), dome-shaped (e.g. FIG. 38) and combinations thereof; arms at any angle to the main body; arms connected to the main body at any distance from the cervical void; arms adjustable in length; arms adjustable in shape; arms with an adjustable and/or malleable stiffener; arms with thicker edges; arms comprised of multiple pieces; arms with varying thicknesses; arms comprising any shape provided that the cross-sectional perimeter does not increase as the distance from the main body increases, allows for intercourse and generally curves towards the mons pubis (contact with the clitoris is not necessary); and arms with none, one or a plurality of grooves, recesses, stiffeners, clitoral exciters, textures and stimulation devices. The shield can have none, one or a plurality of arms.

Protrusion 130—

As illustrated in FIGS. 1-28, 31-44, 48-52, the shield can have an extended portion of material attached to the main body 100: the protrusion 130. The protrusion 130 is located on the same surface of the main body 100 as the cervical void 110. When the shield is in position in the vagina, the protrusion 130 is located adjacent to the vaginal entrance 310 muscles as in FIG. 13. The protrusion 130 is dimensioned to provide additional structure to the main body 100, aiding the shield to deflect the penis away from colliding with the cervix 350. The protrusion 130 aids in retaining the device within the vagina and can apply pressure to the G-spot 330 area for added stimulation. The protrusion 130 further adds volume and fullness within the vagina and tightens the vaginal cavity. The protrusion 130 serves to apply pressure to provide relief from urinary incontinence during intercourse.

Variations of the protrusion 130 comprise: various sized protrusions; protrusions with various cross-sectional geometry comprising: round, oval, rectangular, square, irregular, polygonal, crescent-shaped (e.g. FIGS. 24, 34) and combinations thereof; protrusions in various positions on the main body; protrusions on any surface of the main body; protrusions comprised of multiple pieces; protrusions positioned at any angle to the cervical void (e.g. FIG. 25); protrusions with varying thicknesses; protrusions extending onto the edge of the main body; and any protrusion serving to aid in retaining the shield within the vagina; protrusions having none, one or a plurality of recesses, stiffeners, textures, and stimulation devices. The shield can have none (e.g. FIGS. 29-30), one or a plurality of protrusions.

Groove 140—

Figure 50:
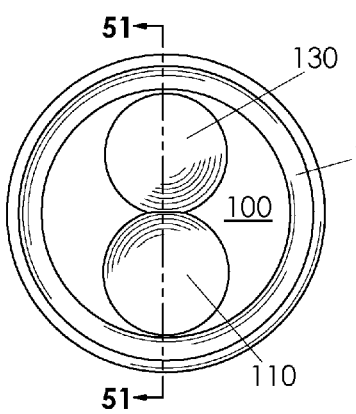
FIG. 50 is a top view of a variation of the shield of FIG. 2 with an alternative main body, an alternative cervical void, no arm, an alternative protrusion and grooves.
Figure 51:
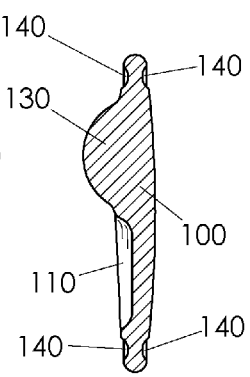
FIG. 51 is a cross-sectional view taken along line 51-51 of the shield of FIG. 50.

As illustrated in FIGS. 50-52 the shield can have a depression alongside the perimeter of the main body 100: the groove 140. The groove 140 is located on both sides of the main body 100 as in FIGS. 51-52. The groove 140 is generally concave in cross-sectional shape. The groove 140 is dimensioned to provide a means for clasping the shield to adjust, position and/or to remove the shield.

Variations of the groove 140 comprise: various sized grooves; grooves with various cross-sectional geometry comprising: circular, oval, rectangular, irregular, polygonal, square and combinations thereof; grooves that are concave or convex; grooves on any surface of the shield; grooves with varying depths; and grooves with any general shape that serve to enable clasping of the shield. The shield can have none, one or a plurality of grooves.

Recess 200—

As illustrated in FIGS. 16-19 the shield can have a removed portion of material within the device: the recess 200. The recess 200 is connected to the cervical void 110. The recess 200 can serve to induce a suction effect within the cervical void 110. With the shield in place within the vagina, the protrusion 130, as in FIGS. 16-17, can be pressed with a finger or an object to expel the air within the recess 200. When the finger or object pressure is removed, the recess 200 naturally attempts to re-inflate due to the elastic nature of the material 200 causing a vacuum effect within the cervical void 110 which aids the cervical void 110 to better adhere to the cervix 350. As the penis moves within the vagina and over the recess 200, the recess 200 is repetitively squeezed to ensure a continual vacuum.

Figure 16:
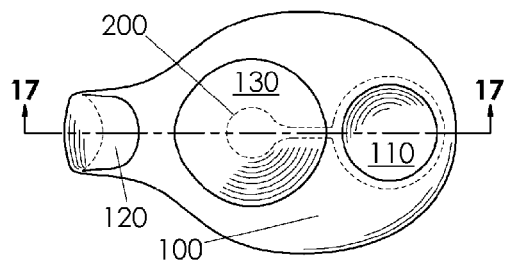
FIG. 16 is a top view of a variation of the shield of FIG. 2 with an alternative main body, an alternative cervical void, an alternative arm, an alternative protrusion and a recess.
Figure 17:
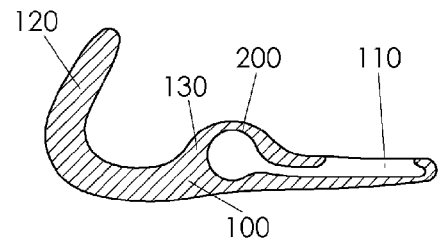
FIG. 17 is a cross-sectional view taken along line 17-17 of FIG. 16.
Figure 18:
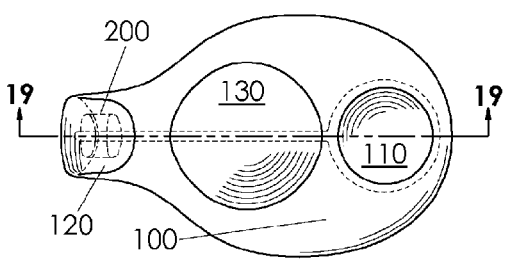
FIG. 18 is a top view of a variation of the shield of FIG. 16 with an alternative recess.
Figure 19:
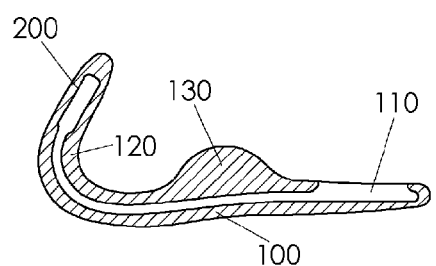
FIG. 19 is a cross-sectional view taken along line 19-19 of FIG. 18.

Alternatively, FIGS. 18-19, illustrate a recess 200 located within the arm 120 and serves the same function as the recess 200 within the protrusion 130 of FIGS. 16-17.

Figure 20:
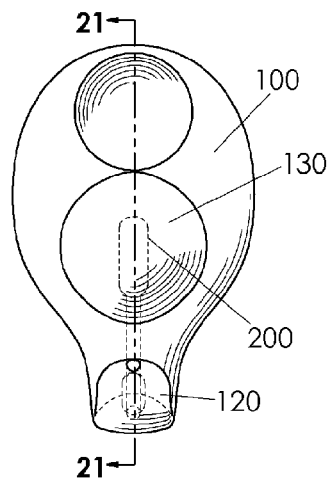
FIG. 20 is a top view of a variation of the shield of FIG. 2 with an alternative main body, an alternative cervical void, an alternative arm, an alternative protrusion and a recess.
Figure 21:
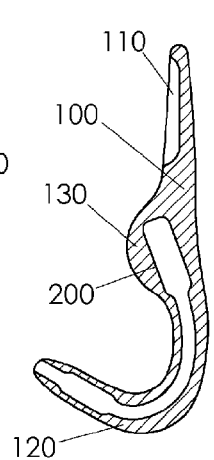
FIG. 21 is a cross-sectional view taken along line 21-21 of FIG. 20.
Figure 22:
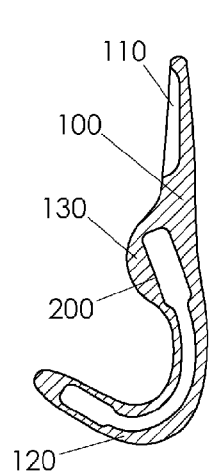
FIG. 22 is a cross-sectional view taken along line 21-21 of the shield of FIG. 20 with an alternative recess.
Figure 23:
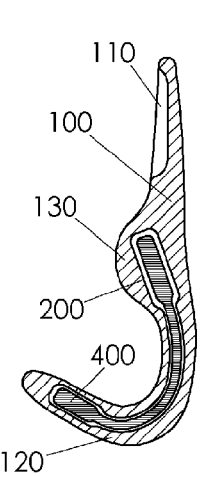
FIG. 23 is a cross-sectional view taken along line 21-21 of the shield of FIG. 20 with an alternative recess having a stimulation device.

Alternatively, FIGS. 20-23 illustrate a recess 200 located within the arm 120 and extending through and into the protrusion 130. FIGS. 20-21 illustrate a recess 200 with expanded areas that serve to hold insertable objects. FIGS. 22-23 illustrate a recess 200 that holds built-in objects such as a stimulation device 400. The recesses 200 are designed to support none, one or a plurality of functions comprising; inducing a vacuum; holding stimulation devices comprising: vibrating devices, pulsating devices, pellet-rotating devices, oscillating devices, heating devices, hard objects, suction devices, motorized devices or any means of stimulation. With the correct choice of materials for the shield, the vibrations, pulses, heating, and/or properties from stimulation devices 400 will be transmitted throughout the shield or in localized regions.

Variations of the recess 200 comprise: recesses piercing through the entire device; recesses having various cross-sectional geometry comprising: circular, polygonal, octagonal or irregular shapes, and combinations thereof; recesses that are arced, straight, parabolic, wavy, or irregular in direction and combinations thereof; recesses with various shaped entry geometry configurations; recesses with or without texture; recesses with none, one, or a plurality of access holes; recesses that connect to other functional elements of the shield; recesses oriented at various angles within the cervical shield; any recess that is dimensioned to create a void within the device for holding none, one, or a plurality of stimulation devices and any recess that is dimensioned to induce a suction. The shield can have none, one, or a plurality of recesses.

Stiffener 210—

Figure 38:
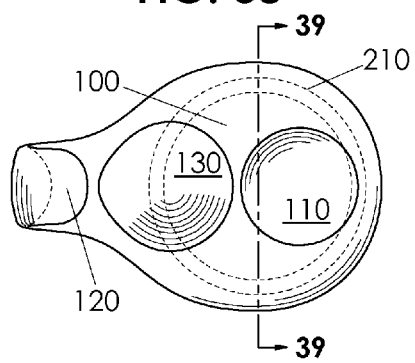
FIG. 38 is a top view of a variation of the shield of FIG. 2 with an alternative main body, an alternative cervical void, an alternative arm, an alternative protrusion and a stiffener.
Figure 39:
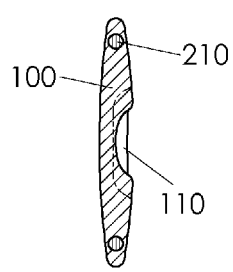
FIG. 39 is a cross-sectional view taken along line 39-39 of FIG. 38.

As illustrated in FIGS. 38-47 the shield can have stiffeners 210. FIGS. 38-39 illustrate an embedded stiffener 210 within the main body 100 of the shield. The stiffener 210 in FIG. 38 is circular and has a circular cross-section (FIG. 39). The stiffener 210 serves to add rigidity to the shield and serves to better transmit vibration from a stimulation device internal or external to the shield. The stiffener's 210 flexural properties are stronger than the shield material properties. The stiffener 210 is comprised of a more dense material and therefore, aids the unfurling of the shield. The stiffener 210 provides structure to the device ensuring that the device continually flexes to apply pressure to the vaginal walls aiding in retaining the shield within the vagina. Complete unfurling within the vagina is not necessary.

Figure 41:
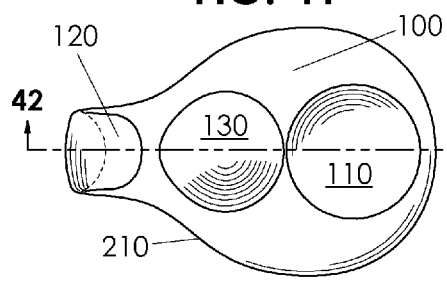
FIG. 41 is a top view of a variation of the shield of FIG. 2 with an alternative main body, an alternative cervical void, an alternative arm, an alternative protrusion and a stiffener.
Figure 42:
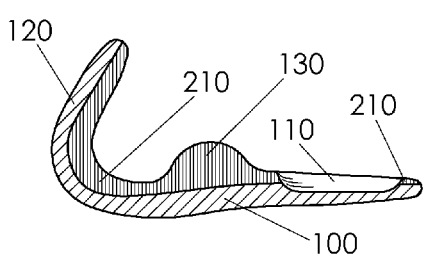
FIG. 42 is a cross-sectional view taken along line 42-42 of FIG. 41.

Alternatively, FIGS. 41-42 illustrate a stiffener 210 that is a layer of the shield. Additionally, this stiffener 210 provides structure to the entire device to aid in holding the device's shape and improving the flexural strength properties of the device to resist movement during use.

Figure 43:
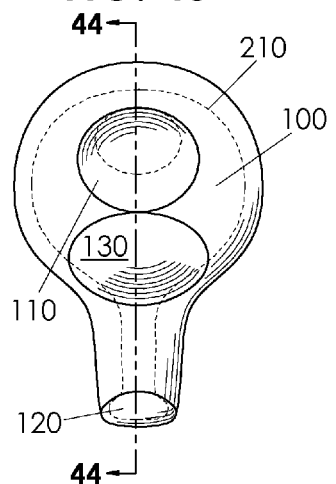
FIG. 43 is a top view of a variation of the shield of FIG. 2 with an alternative main body, an alternative cervical void, an alternative arm, an alternative protrusion and a stiffener.
Figure 44:
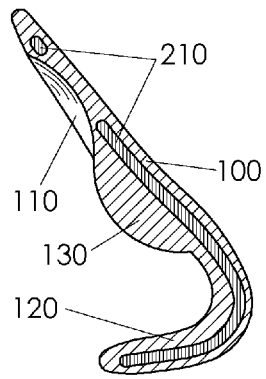
FIG. 44 is a cross-sectional view taken along line 44-44 of FIG. 43.
Figure 45:
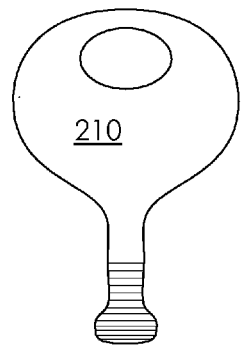
FIG. 45 is a top view of the stiffener that is embedded in the shield of FIGS. 43-44.

Alternatively, FIGS. 43-45 illustrate a stiffener 210 that is embedded within the main body 100 and the arm 120 of the shield.

Figure 46:
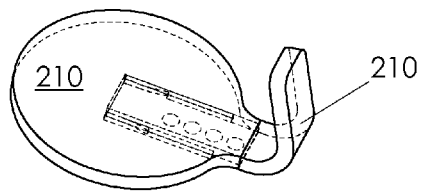
FIG. 46 is an isometric view from above of a two part adjustable stiffener in a collapsed position.
Figure 47:
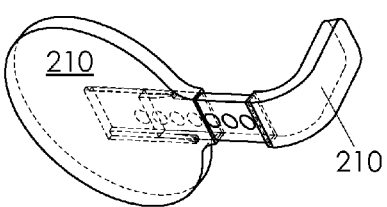
FIG. 47 is an isometric view from below of a two part adjustable stiffener in an expanded position.
Figure 48:
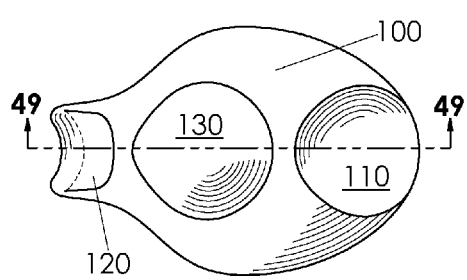
FIG. 48 is a top view of a variation of the shield of FIG. 2 with an alternative main body, an alternative cervical void and an alternative protrusion.
Figure 49:
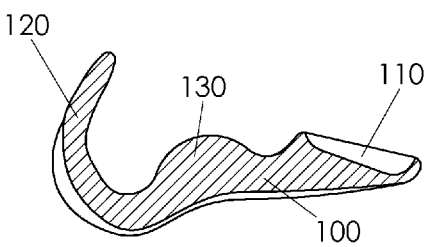
FIG. 49 is a cross-sectional view taken along line 49-49 of FIG. 48.

Alternatively, FIGS. 46-47 illustrate a position-adjustable stiffener 210 for a shield. FIG. 46 is a view of the stiffener 210 in a collapsed state while FIG. 47 is a view of the stiffener 210 in an expanded state. The material properties of the shield are elastic and accommodate an adjustable stiffener 210.

Variations of the stiffener 210 comprise: various sized stiffeners; stiffeners with various cross-sectional geometry comprising: round, polygonal, crescent-shaped, irregular, elliptical, dome-shaped and combinations thereof; stiffeners of varying thicknesses; stiffeners of varying shapes (e.g. W-shaped, FIG. 40); stiffeners made with multiple materials; stiffeners comprised of multiple pieces; stiffeners that serve to aid in maintaining, reinforcing and supporting the shape of any part of the device and/or serve to transmit the vibration from an object or a stimulation device. The shield can have none, one, or a plurality of stiffeners.

Clitoral Exciter 220—

As illustrated in FIGS. 27-28, the shield can have a generally elliptical depression near the end of the arm 120: the clitoral exciter 220. The clitoral exciter 220 is located on the same surface of the shield as the cervical void 110. The clitoral exciter 220 is a section of material removed from the arm 120. The clitoral exciter 220 is dimensioned to cover a portion of the clitoris 300, providing a positioning means and a stimulation means. The clitoral exciter 220 serves to aid in preventing the arm 120 from sliding to one side of the clitoris 300 and further serves to increase the amount of stimulation by covering a larger area of the clitoris 300.

Variations of the clitoral exciter 220 comprise: exciters of various sizes; exciters with geometric concave/convex shapes comprising: irregular, polygonal, round, elliptical and combinations thereof; exciters of various depths/extensions; exciters with various edge geometries; exciters lined with an alternate material; exciters with texture; exciters with none, one or a plurality of recesses; and exciters that can be any shape that serve to increase, concentrate or disperse the contact area of the arm on the clitoris. The shield can have none, one or a plurality of clitoral exciters.

Texture 230—

As illustrated in FIGS. 31-37, the shield can have texture 230. This texture 230 is shown as raised ridges. The texture 230 on the arm 120 serves to stimulate the clitoris 300. The texture 230 on the bottom side of the main body 100 serves to stimulate the penis. Texture 230 can serve to help retain the shield in position on the wearer and/or serve to induce a greater level of stimulation.

Variations of texture 230 comprise: round half spheres, dimples, finger-like projections, any means of changing the feel, flexibility or consistency of any surface and any configurations/combinations of texture, texture on any surface of the shield; texture that can create a groove; and any means of changing the feel or material consistency of any surface on the shield. The shield can have no texture.

Material

The shield, excluding the stiffeners, is made of at least one elastomeric material comprising: medical-grade silicones, rubbers, elastomeric gels, etc. The elastomeric material for the shield has a durometer between 0.01-10 on the Shore 00 scale of hardness. However, the shield can be made with any material that comprises the following characteristics. The material should be soft, elastic, flexible and deformable by human fingers without permanent deformation. The material should also be stable and capable of multiple washings without deterioration. The material should also have the density and tactile feel of human flesh and be capable of readily transmitting sensations throughout. The material should have elastic memory to prevent permanent deformation and allow the device to naturally unroll after insertion into the vagina. The flexural properties of the material provide the means for retaining the device within the vagina.

An additional material is required for the stiffener 210. The preferred material for the manufacture of the stiffener 210 is at least one elastomeric material comprising: medical-grade silicones, rubbers, elastomeric gels, etc. with a durometer between 0.1-50 on the Shore A scale of hardness. The stiffener 210 is preferably constructed from a similar material with similar properties used for the shield, albeit more rigid. The rigidity of the stiffener 210 is dependent upon the thickness and the durometer of the material used. A thicker stiffener 210 having a lower durometer material can have the same rigidity and flexural properties as a thinner stiffener 210 having a higher durometer material. Material with durometers outside of the stated preferred range of durometers can be used depending on the shape, geometry and characteristics for the stiffener 210. Alternatively, the stiffener 210 can be made of any type of material comprising: metal, plastic, etc. that is more rigid than the material for the shield.

Manufacturing

The shield is molded using conventional injection molding techniques and technologies.

The stiffener 210 can be manufactured using industry standard injection molding technologies and techniques. However, the stiffener 210 can also be a standard off-the-shelf silicone O-ring as in FIGS. 38-39.

Shields with stiffeners 210, as in FIGS. 38-44 are manufactured using conventional injection over-molding/co-molding techniques and technologies.

Operation

As illustrated in FIGS. 6-9, the main body 100 is rolled up with the cervical void 110 on the outside. The rolled main body 100 is then inserted into the vagina with the cervical void 110 entering the vagina first. Once the rolled up main body 100 passes the vaginal entrance 310, due to the shield's resiliency, the shield will unroll as in FIGS. 10-13, retaining the device within the vaginal cavity. However, complete unfurling is not necessary for the shield to function as intended (see placement in vagina FIGS. 12-13). The cervical void 110 positioned on the cervix 350 aids in stabilizing and aligning the device within the vagina. Furthermore, for shields with an arm 120, the arm 120 resides in close proximity to the clitoris 300 and displacements for comfort can be performed by clasping the arm 120 and adjusting accordingly. In position, the shield prevents the penis from striking the cervix 350 and guides the penis away from the anterior vaginal wall 320.

To remove, the shield is clasped and pulled out of the vagina. Due to the shape and the deformability of the main body 100, the device naturally coils to allow the shield to be removed. The shield can then be cleaned and reused. Furthermore, for shields with an arm 120, the arm 120 is clasped and the shield is pulled out of the vagina.

CONCLUSION, RAMIFICATIONS AND SCOPE

Accordingly, the reader will see that the cervical shield protects the cervix from collision by the penis and provides a channel to guide the penis away from the cervix. This shield provides women who suffer from collision dyspareunia a new, highly effective, economical and non-surgical means allowing for more comfortable deeper penetrating intercourse.

While the above figures contain many specificities, the reader should not construe these as limitations on the scope of the invention, but merely as exemplifications of several preferred embodiments thereof. Various other embodiments are possible. Further embodiments of the cervical shield sexual aid device comprising various configurations of the variations described for each element in the specification are possible. Those element variations include variations of: main bodies, cervical voids, arms, protrusions, grooves, recesses, stabilizers, clitoral exciters, textures and stimulation devices. Different flexible and resilient materials can be used for the cervical shield device. The shield can be used by a single user or couples. A shield can have multiple cervical voids of various sizes to accommodate different sized cervixes. The elements can have different shape geometry to create various sensations on the penis and on the wearer. The cervical shield can have a skin or cover added to the entire device or a portion of the device to change the shape or size of any element on the device. Pigments, scents, pharmacological compounds or transdermal medication can be placed onto or added to the material of the shield. The shield can be worn for extended periods of time. The cervical shield can be designed and constructed to be symmetrical or asymmetrical. The shield can be made of multiple materials. Optionally, tentacle-like protrusions, offering additional stimulation, spanning from the device can be added. These tentacle-like protrusions can touch sensitive regions of the body. The reader can see that the cervical shield device provides individuals and/or couples with a new, highly effective and economical means to enjoy more comfortable deeper penetrating intercourse.

I claim:

1. A sexual aid article, comprising:
    a) a main body;
    b) at least one void of material, defined in a portion of the main body,
        wherein the main body comprises at least one elastomeric material,
        the main body is dimensioned for placement inside a human vagina,
        the main body is configured to be inserted into the vagina in a generally coiled configuration,
        the main body is configured to uncoil and expand to press and apply pressure against vaginal walls, and
        the at least one void is dimensioned to shield a human cervix; and
    c) at least one elongated arm,
        wherein the at least one elongated arm is connected to the main body,
        a perimeter of a cross-section of the at least one elongated arm does not increase as a distance from the main body increases,
        the at least one elongated arm is configured to reach outside the vagina for adjusting, positioning or removing the article and to substantially curve outside of the vagina towards the at least one void when the main body is inserted into the vagina with the at least one void shielding the cervix,
        the main body is a generally flattened shape dimensioned for coiling into a cylinder with the at least one void on the outside of the cylinder,
        the main body is configured to create a concave channel along an anterior vaginal wall a length of the vagina, and
        the main body is configured for flexing against the anterior vaginal wall, stretching the vagina into an elliptical cylinder the length of the vagina;
    whereby the sexual aid article shields the cervix and guides a real or an artificial human penis away from the cervix during intercourse.

2. The sexual aid article of claim 1, wherein the main body is solid.

3. The sexual aid article of claim 1, wherein the generally flattened shape is selected from the group of shapes consisting of: round, hourglass, diamond, irregular, U, elliptical, oval, triangular, square, rectangular, polygonal, and spade shapes.

4. The sexual aid article of claim 1, wherein the main body further comprises at least one protrusion,
    wherein the at least one protrusion extends from the main body,
    the at least one protrusion is dimensioned to contact the anterior vaginal wall,
    the at least one protrusion is dimensioned to retain the main body inside the vagina,
    and the at least one protrusion is positioned between the at least one void and an edge of the main body.

5. The sexual aid article of claim 1, further comprising at least one recess.

6. The sexual aid article of claim 5, wherein the at least one recess further comprises at least one stimulation means.

7. The sexual aid article of claim 1, wherein the at least one void further comprises at least one suction means.

8. The sexual aid article of claim 1, further comprising at least one stiffener wherein the at least one stiffener is capable of restricting the deformation of the sexual aid article.

9. The sexual aid article of claim 8, wherein the at least one stiffener is adjustable for size.

10. A method for shielding a cervix and guiding a real or an artificial human penis away from the cervix during intercourse, comprising:
   a) providing a cervical shield comprising
      a main body that has a generally flattened shape;
      at least one void of material, defined in a portion of the main body,
         wherein the main body comprises at least one elastomeric material,
         the main body is dimensioned for placement inside a human vagina,
         the main body is configured to be inserted into the vagina in a generally coiled configuration,
         the main body is configured to uncoil and expand to press and apply pressure against vaginal walls,
         the at least one void is dimensioned to shield a human cervix and
      at least one elongated arm,
         wherein the at least one elongated arm is connected to the main body, a perimeter of a cross-section of the at least one elongated arm does not increase as a distance from the main body increases,
         the at least one elongated arm is configured to reach outside the vagina for adjusting, positioning or removing the cervical shield and to substantially curve outside of the vagina towards the at least one void when the main body is inserted into the vagina with the at least one void shielding the cervix,
      the main body is configured to create a concave channel along an anterior vaginal wall a length of the vagina, and
      the main body is configured for flexing against the anterior vaginal wall, stretching the vagina into an elliptical cylinder the length of the vagina,
   b) rolling the main body of the cervical shield into a cylinder with the at least one void on an outside of the cylinder,
   c) inserting the cervical shield into the vagina and letting the main body naturally unroll once clear of a vaginal entrance so that the main body is retained by the vaginal entrance,
   d) adjusting the placement of the cervical shield to fit the at least one void onto the cervix.

11. The method of claim 10, wherein the main body of the cervical shield is solid.

12. The method of claim 10, wherein the generally flattened shape is selected from the group of shapes consisting of: round, hourglass, irregular, U, elliptical, oval, triangular, square, rectangular, polygonal, and spade shapes.

13. The method of claim 10, wherein the cervical shield further comprises at least one protrusion,
   wherein the at least one protrusion extends from the main body,
   the at least one protrusion is dimensioned to contact the anterior vaginal wall,
   the at least one protrusion is dimensioned to retain the main body inside the vagina,
   and the at least one protrusion is positioned between the at least one void and an edge of the main body.

14. The method of claim 10, wherein the cervical shield further comprises at least one recess.

15. The method of claim 14, wherein the at least one recess further comprises at least one stimulation means.

16. The method of claim 10, wherein the at least one void further comprises at least one suction means.

17. The method of claim 10, wherein the cervical shield further comprises at least one stiffener wherein the at least one stiffener is capable of restricting the deformation of the cervical shield.

18. The method of claim 17, wherein the at least one stiffener is adjustable for size.

* * * * *